(12) United States Patent
Yamashita et al.

(10) Patent No.: US 7,638,647 B2
(45) Date of Patent: Dec. 29, 2009

(54) METHOD FOR PREPARING (E3,Z5)-3,5-ALKADIENYL ACETATE

(75) Inventors: Miyoshi Yamashita, Joetsu (JP); Takehiko Fukumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/323,823

(22) Filed: Nov. 26, 2008

(65) Prior Publication Data

US 2009/0143617 A1 Jun. 4, 2009

(30) Foreign Application Priority Data

Nov. 30, 2007 (JP) ............................ 2007-309892

(51) Int. Cl.
*C07C 67/02* (2006.01)
(52) U.S. Cl. ..................................... 560/261
(58) Field of Classification Search ........................ None
See application file for complete search history.

(56) References Cited

OTHER PUBLICATIONS

Unelius et al., Identification and Synthesis of the Sex Pheromone of *Phtheochroa cranaodes* (Lepidoptera: Tortricidae), *Tetrahedron Letter*, vol. 37, No. 9, pp. 1505-1508 (1996).
Coracini et al., Behavioural effects of minor sex pheromone components in Brazilian apple leafroller *Bonagota cranaodes* (Lep., Tortricidae), *J. Appl. Ent.*, 127, pp. 427-434 (2003).
Kocienski, "Protecting Groups", Foundations of Organic Chemistry Series, pp. 22-29, 82-85.

*Primary Examiner*—Paul A Zucker
(74) *Attorney, Agent, or Firm*—Alston & Bird LLP

(57) ABSTRACT

Provided is a method for preparing (E3,Z5)-3,5-alkadienyl acetate and (E3,Z5)-3,5-dodecadienyl acetate which is a sex pheromone of Brazilian apple leafminer. Specifically, provided is a method for preparing (E3,Z5)-3,5-alkadienyl acetate, comprising steps of hydrolyzing 5,5-diethoxy-(Z3)-3-pentenyl methoxymethyl ether in the presence of an acid to obtain 4-formyl-(E3)-butenyl methoxymethyl ether; reacting the 4-formyl-(E3)-butenyl methoxymethyl ether with alkylidene triphenylphosphorane in accordance with the Wittig reaction to obtain (E3,Z5)-3,5-alkadienyl methoxymethyl ether; and obtaining (E3,Z5)-3,5-alkadienyl acetate using the (E3,Z5)-3,5-alkadienyl methoxymethyl ether as a starting substance.

3 Claims, No Drawings

METHOD FOR PREPARING (E3,Z5)-3,5-ALKADIENYL ACETATE

BACKGROUND OF THE INVENTION

1. Field of the Invention

The present invention relates to a method for preparing (E3,Z5)-3,5-dodecadienyl acetate, a sex pheromone component of Brazilian apple leafminer (*Bonagota cranaodes*) which is an apple pest in South American countries such as Brazil and Uruguay.

2. Description of the Related Art

Brazilian apple leafminer is one of major apple pests in South American countries such as Brazil and Uruguay and damage caused thereby has become a problem in recent years. Pesticides are used for control of Brazilian apple leafminer but their effect is not sufficient. There is accordingly a demand for the development of a new control method satisfactory from the viewpoint of the global environment and human health.

It has been elucidated (C. R. Unelius, et al., *Tettrahedron Lett.*, 37, 1505(1996)) by C. Ricard Unelius, et al., in 1996 that the sex pheromone of Brazilian apple leafminer has (E3,Z5)-3,5-dodecadienyl acetate as a main component thereof. In addition, M. D. A. Coracini, et al., has reported that (E3,Z5)-3,5-tetradecadienyl acetate is one of subsidiary components of the sex pheromone of the insect and it is therefore known that (E3,Z5)-3,5-alkadienyl acetates having conjugated double bonds which are a double bond with E configuration at the 3-position and a double bond with Z configuration at the 5-position, each counted from the terminal acetoxyl group, are effective as a sex pheromone of Brazilian apple leafminer (M. D. A. Coracini, *J. Appl. Ent.*, 127, 427 (2003)).

Protecting groups of an alcohol industrially used in a large amount typically include an acetyl group (Protecting Groups., P. J. Kocienski, Georg Thieme Verlag Stuttgart: New York, P22(1994)), a 1-ethoxyethyl group (Protecting Groups., P. J. Kocienski, Georg Thieme Verlag Stuttgart: New York, P84(1994)), and a tetrahydropyranyl group (Protecting Groups., P. J. Kocienski, Georg Thieme Verlag Stuttgart: New York, P84(1994)).

SUMMARY OF THE INVENTION

The present invention provides a method for preparing (E3,Z5)-3,5-alkadienyl acetate and (E3,Z5)-3,5-dodecadienyl acetate, a sex pheromone of Brazilian apple leafminer.

In the preparation of (E3,Z5)-3,5-alkadienyl acetate having conjugated double bonds which are a double bond with an E configuration at the 3-position and a double bond with a Z configuration at the 5-position, each counted from the terminal acetoxyl group, use of 3-butyn-1-ol having a triple bond at the 3-position from the terminal alcohol group as a starting substance may be considered. Since the method for preparing (E3,Z5)-3,5-alkadienyl acetate by using this 3-butyn-1-ol as a starting substance requires a step of using a carboanion or the like which is adversely affected by an alcohol group, the terminal alcohol group of 3-butyn-1-ol must be protected.

It has been found by the present inventors that an acetal portion of 5,5-diethoxy-(Z3)-3-pentenyl methoxymethyl ether, which can be produced by using 3-butyn-1-ol as a starting substance and protecting the alcohol portion thereof with a methoxymethyl group by using dimethoxymethane which is inexpensive and available in a large amount, can be selectively hydrolyzed with an acid without elimination of the alcohol protecting group and even the Wittig reaction between the resulting 4-formyl-(E3)-3-butenyl methoxymethyl ether and alkylidene phosphorane scarcely generates the corresponding 1,3,5-alkatriene which will otherwise be formed by the elimination reaction. It has also been found that the subsequent deprotection reaction proceeds in a markedly good yield and an intended (E3,Z5)-3,5-alkadienyl acetate can be prepared efficiently, leading to the completion of the present invention.

In the present invention, there is provided a method for preparing (E3,Z5)-3,5-alkadienyl acetate, comprising steps of:

hydrolyzing 5,5-diethoxy-(Z3)-3-pentenyl methoxymethyl ether in the presence of an acid to obtain 4-formyl-(E3)-3-butenyl ether;

reacting the 4-formyl-(E3)-3-butenyl methoxymethyl ether with alkylidene triphenylphosphorane in accordance with the Wittig reaction to obtain (E3,Z5)-3,5-alkadienyl methoxymethyl ether; and obtaining (E3,Z5)-3,5-alkadienyl acetate from the E3,Z5)-3,5-alkadienyl methoxymethyl ether.

The alkylidene triphenylphosphorane may be represented as a preferable example by

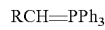

RCH=PPh₃ wherein R represents a group having from 4 to 12 carbon atoms, especially from 6 or 8 carbon atoms and Ph represents a phenyl group, and (E3,Z5)-3,5-alkadienyl methoxymethyl ether may be represented as a preferable example by

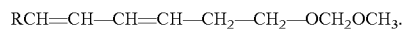

RCH=CH—CH=CH—CH₂—CH₂—OCH₂OCH₃.

According to the present invention, (E3,Z5)-3,5-alkadienyl acetate and (E3,Z5)-3,5-dodecadienyl acetate, which is a sex pheromone of Brazilian apple leafminer, can be prepared efficiently under industrially mild conditions.

DETAILED DESCRIPTION OF THE PREFERRED EMBODIMENTS

The preparation method of the present invention will hereinafter be described in detail.

First, 5,5-diethoxy-(Z3)-3-pentenyl methoxymethyl ether to be used as a starting substance can be obtained, for example, by reacting 3-butyn-1-ol with dimethoxymethane to obtain 3-butynyl methoxymethyl ether, reacting the 3-butynyl methoxymethyl ether with methylmagnesium chloride and then, with ethyl orthoformate to obtain 5,5-diethoxy-3-pentynyl methoxymethyl ether, and then subjecting the 5,5-diethoxy-3-pentynyl methoxymethyl ether to catalytic hydrogenation.

More specifically, 3-butyn-1-ol can be prepared readily, for example, in accordance with the following known method:

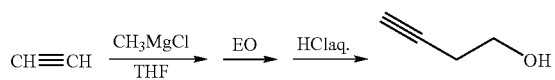

$$CH\equiv CH \xrightarrow[\text{THF}]{\text{CH}_3\text{MgCl}} \xrightarrow{\text{EO}} \xrightarrow{\text{HClaq.}} \diagup\!\!\!\diagdown\text{OH}$$

wherein THF represents tetrahydrofuran and EO represents ethylene oxide.

3-butyn-1-ol (1) can be reacted with dimethoxymethane in the presence of, for example, para-toluenesulfonic acid and lithium bromide, to produce 3-butynyl methoxymethyl ether (2), protecting the alcohol group. In this reaction, it is preferable to use 0.1 to 1.0 mol of para-toluenesulfonic acid, 0.1 to 0.5 mol of lithium bromide and 3.5 to 5.0 mol of dimethoxymethane per mol of 3-butyn-1-ol (1). The reaction temperature may be desirably from 30 to 45° C.

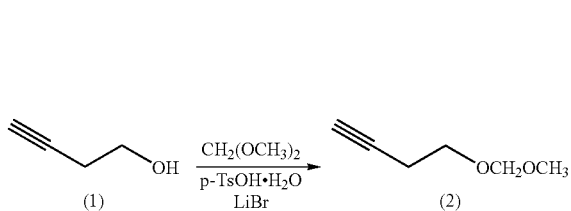

wherein p-TsOH.H$_2$O represents p-toluenesulfonic acid monohydrate.

3-butynyl-methoxymethyl ether (2) can be reacted with methylmagnesium chloride and then with ethyl orthoformate to produce 5,5-Diethoxy-3-pentynyl-methoxymethyl ether (3). The following method may be included by a preferable example.

First, a tetrahydrofuran solution of methylmagnesium chloride is prepared using methyl chloride and metal magnesium in tetrahydrofuran in a known manner. Then, 3-butynyl methoxymethyl ether (2) is added dropwise to the resulting solution and reacted at preferably from 60 to 80° C. Ethyl orthoformate and toluene are then added. The resulting mixture has tetrahydrofuran distilled off by heating, and then reacted at preferably 80 to 95° C. to obtain 5,5-diethoxy-3-pentynyl methoxymethyl ether (3). In these reactions, amounts of methylmagnesium chloride and ethyl orthoformate are preferably 1.1 to 1.3 mol and 1.2 to 1.4 mol, respectively, and those of tetrahydrofuran and toluene are preferably 300 to 500 g and 250 to 300 g, respectively, per mol of 3-butynyl methoxymethyl ether (2).

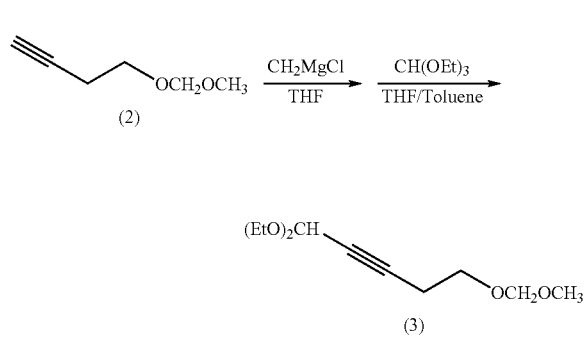

wherein Et represents an ethyl group and THF represents tetrahydrofuran.

Catalytic hydrogenation of the triple bond of 5,5-diethoxy-3-pentynyl methoxymethyl ether (3) can be reduced into a (Z)-double bond to produce 5,5-Diethoxy-(Z3)-3-pentenyl methoxymethyl ether (4).

Examples of the catalyst used for the reaction may include palladium-carbon, palladium-alumina, Lindlar catalyst, Raney nickel and P2-nickel. Of these, P2-nickel is especially preferred. In order to prevent excessive hydrogenation, amine such as pyridine, quinoline or ethylenediamine may be added for the reaction. The hydrogen pressure may be preferably from normal pressure to 0.5 MPa, while the reaction temperature may be preferably from 30 to 50° C.

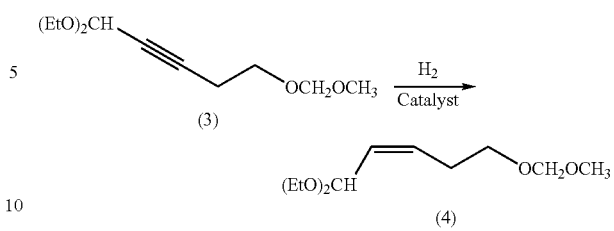

wherein Et represents an ethyl group.

Addition of an acid (preferably, an aqueous solution of hydrogen chloride) to 5,5-dimethoxy-(Z3)-3-pentenyl methoxymethyl ether (4), for example, preferably in toluene or n-hexane, can have a diethylacetal portion of the compound hydrolyzed into an aldehyde, more specifically, an α,β-unsaturated aldehyde, thereby isomerizing the double bond into a more stable E configuration to produce 4-formyl-(E3)-3-butenyl methoxymethyl ether (5). In this reaction, the aqueous solution of hydrogen chloride may have a concentration of preferably from 5 to 10% by weight and be added in an amount of preferably from 100 to 130 g per mol of 5,5-dimethoxy-(Z3)-3-pentenyl-methoxymethyl ether (4). The reaction temperature may be preferably from 10 to 20° C.

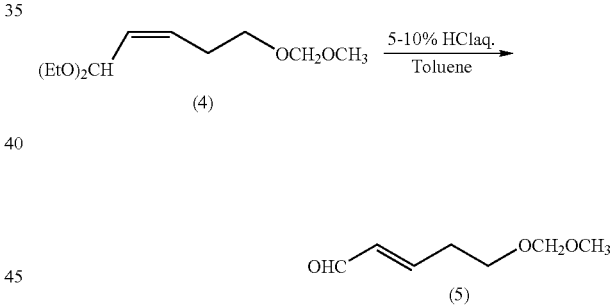

wherein Et represents an ethyl group.

4-Formyl-(E3)-3-butenyl methoxymethyl ether (5) can be reacted with alkylidene triphenylphosphorane (7) in accordance with the Wittig reaction to produce (E3,Z5)-3,5-alkadienyl methoxymethyl ether (8).

For example, the alkylidene triphenylphosphorane (7) may be synthesized by reacting alkyl bromide with triphenylphosphine in dimethylformamide in a known manner to prepare a dimethylformamide solution of alkyltriphenylphosphonium bromide (6), adding tetrahydrofuran thereto, and then adding potassium t-butoxide to the resulting mixture. Then, the (E3, Z5)-3,5-alkadienyl methoxymethyl ether (8) may be obtained by adding 4-formyl-(E3)-3-butenyl methoxymethyl ether (5) dropwise to the alkylidene triphenylphosphorane (7) for forming a (Z)-double bond in accordance with the Wittig reaction. An amount of 1,3,5-alkatriene produced as a by-product of an elimination reaction is as low as 2.0% or less.

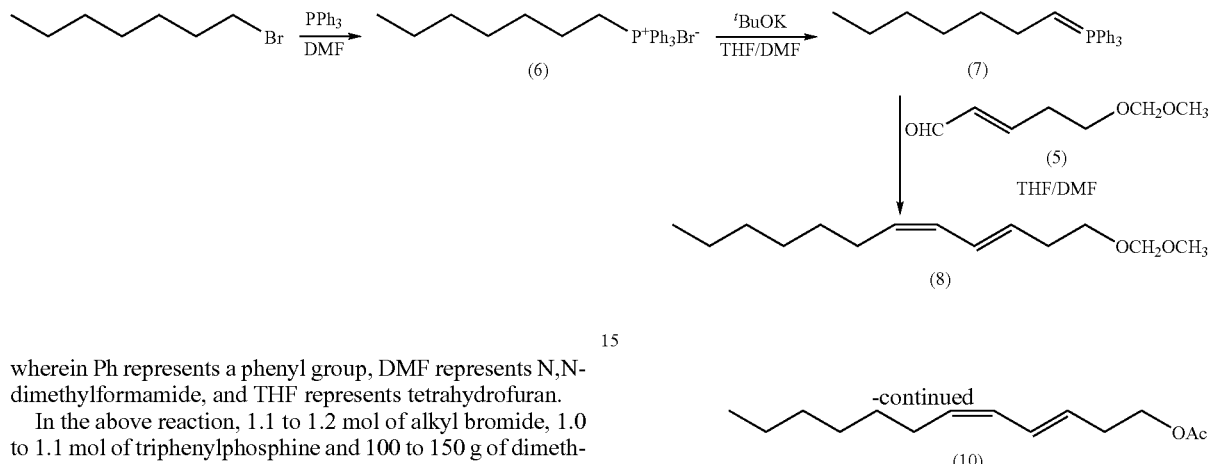

wherein Ph represents a phenyl group, DMF represents N,N-dimethylformamide, and THF represents tetrahydrofuran.

In the above reaction, 1.1 to 1.2 mol of alkyl bromide, 1.0 to 1.1 mol of triphenylphosphine and 100 to 150 g of dimethylformamide may be preferably used per mol of 4-formyl-(E3)-3-butenyl methoxymethyl ether (5). In the phosphorane synthesis reaction, 1.00 to 1.03 mol of potassium t-butoxide may be preferably used per mol of 4-formyl-(E3)-3-butenyl methoxymethyl ether (5). The reaction temperature may be preferably from 15 to 20° C. The Wittig reaction can be preformed at the reaction temperature of −70 to 30° C., particularly preferably −15 to −10° C.

The (E3,Z5)-3,5-alkadienyl methoxymethyl ether (8) can be treated with an acid to produce (E3,Z5)-3,5-alkadienol (9).

For example, the (E3,Z5)-3,5-alkadienol (9) can be obtained by reacting the (E3,Z5)-3,5-alkadienyl methoxymethyl ether (8) with an aqueous solution of hydrogen chloride in methanol to deprotect the methoxymethyl group. The reaction can proceed smoothly by distilling off dimethoxymethane, a by-product of the reaction, in a distillation tower attached to the reactor and no isomerization of the EZ mixture can be confirmed during the reaction.

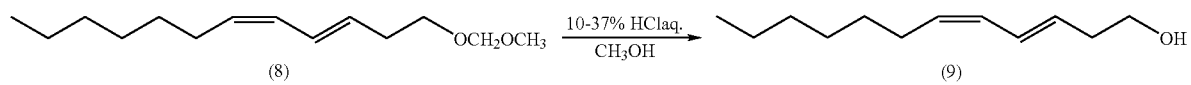

wherein Ac represents an acetyl group.

In the above reaction, 0 to 200 g of toluene and 1.1 to 1.3 mol of acetic anhydride may be preferably used per mol of the (E3,Z5)-3,5-alkadienol (9). The catalyst may be an ordinarily used one such as pyridine, triethylamine or dimethylaminopyridine. The reaction temperature may be desirably from 6 to 70° C.

EXAMPLE 1

<Preparation of 4-formyl-(E3)-3-butenyl methoxymethyl ether>

A concentrated solution of 5,5-dimethoxy-(Z)-3-pentenyl methoxymethyl ether was dissolved in toluene (80.0 g). The resulting solution was placed in a reactor and stirred at from 10 to 15° C. An 8% by weight aqueous solution of hydrogen chloride was added dropwise thereto at 15 to 20° C., and the mixture was stirred for one hour. After stirring, the reaction mixture was extracted with toluene (200 g). The water phase was removed, while the organic phase was washed with brine and an aqueous solution of sodium bicarbonate.

The organic phase thus obtained was concentrated under reduced pressure by removing the solvent. The residue was distilled under reduced pressure to yield 4-formyl-(E3)-3-butenyl methoxymethyl ether (bp: 65 to 66° C. [2 mmHg], 152.16 g, 1.06 mol) in a yield of 84.0%.

[Nuclear magnetic resonance spetrum] $^1$H-NMR (300 MHz, CDCl$_3$): δ 2.60(2H, dt), 3.32(3H, s), 3.67(2H, t), 4.60 (2H, s), 6.16(12H, dd), 6.85(1H, dt), 9.49(1H, d); $^{13}$C-NMR (75.6 MHz, CDCl$_3$): δ 32.94, 55.27, 65.42, 96.41, 134.20, 154.81, 193.71

[Mass Spectrum] EI-mass spectrum (70 eV): m/z 114(M$^+$), 83, 75, 55, 45; CI mass spectrum (isobutane): 115 (M+H)

<Preparation of (E3,Z5)-3,5-dodecadienyl methoxymethyl ether>

Triphenylphosphine (105.02 g, 0.40 mol), n-heptyl bromide (76.93 g, 0.43 mol) and N,N-dimethylformamide (82.0

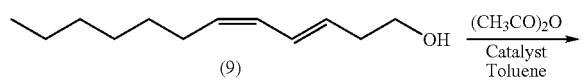

g) were placed in a reactor and stirred at 105 to 110° C. for 26 to 30 hours. After stirring, the reaction mixture was cooled to 20° C. and tetrahydrofuran (370.0 g) and potassium t-butoxide (42.10 g, 0.375 mol) were added thereto successively at 10 to 15° C. The resulting mixture was stirred at 20° C. for one hour. After stirring, the reaction mixture was cooled to −20° C. and 4-formyl-(E3)-3-butenyl methoxymethyl ether (52.47 g, 0.364 mol) was added dropwise thereto at −15 to −5° C.

After dropwise addition was over, the temperature of the mixture was raised to the range of 20 to 25° C. over one hour and then the mixture was stirred as it was for one hour. Then water (200 g) was added thereto to terminate the reaction. The reaction mixture was extracted with toluene (200 g). The organic phase was washed with water and then concentrated under reduced pressure by removing toluene.

After concentration, n-hexane (250 g) was added and triphenylphosphine oxide thus precipitated was separated by filtration. The filtrate was concentrated under reduced pressure again and the concentrate was distilled under reduced pressure to yield intended (E3,Z5)-3,5-dodecadienyl methoxymethyl ether (bp: from 82 to 86° C. [1 mmHg], 52.98 g, 0.23 mol) in a yield of 65.2%.

Gas chromatography (DB-5: 30 m×0.25 mmϕ, temperature elevation from 150° C. to 280° C. at a rate of 10° C./min) revealed that as a result of the Wittig reaction, a 1,3,5-alkatriene content was 1.32% and an EZ:EE isomer ratio was 89.33:10.67.

[Mass Spectrum] EI-mass spectrum (70 eV): m/z 226 (M$^+$), 164, 138, 110, 95, 81, 67, 55

<Preparation of (E3,Z5)-3,5-dodecadienol>

(E3,Z5)-3,5-Dodecadienyl methoxymethyl ether (54.55 g, 0.241 mol) and methanol (300.84 g) were placed in a reactor equipped with a distillation tower and stirred at 22 to 25° C. A 20% by weight aqueous solution (135 g) of hydrogen chloride was added dropwise thereto at 25 to 30° C. over one hour.

After dropwise addition, the temperature of the reaction mixture was raised to 60° C. and stirred for one hour. By gradually reducing the pressure to 450 mmHg, a mixture of dimethoxymethane and methanol produced as a by-product was distilled off from the distillation tower. The residue was stirred for 5 hours. After stirring, the reaction mixture was cooled to 25° C. and extracted with toluene (200 g). The organic phase was washed with brine and an aqueous solution of sodium bicarbonate. The solvent was removed under reduced pressure to yield a concenetrated solution (62.82 g, 73.16%) of (E3,Z5)-3,5-dodecadienol. The resulting concentrated solution was provided for the subsequent reaction without purification.

It was revealed by gas chromatography (DB-5: 30 m×0.25 mmϕ, temperature elevation from 150° C. to 280° C. at a rate of 10° C./min) that an EZ:EE isomer ratio was 91.24:8.75.

[Mass Spectrum] EI-mass spectrum (70 eV): m/z 182 (M$^+$), 109, 95, 79, 67; CI mass spectrum (isobutane): 183 (M+H)

<Preparation of (E3,Z5)-3,5-dodecadienyl acetate>

A concentrated solution (62.82 g, 73.16%) of (E3,Z5)-3, 5-dodecadienol, toluene (150 g), acetic anhydride (10 g, 0.098 mol) and dimethylaminopyridine (1.0 g) were placed in a reactor and stirred at 50 to 60° C. Acetic anhydride (23.45 g, 0.23 mol) was added dropwise thereto at 65 to 70° C. over 30 minutes, followed by stirring at 75° C. for one hour.

After stirring, the reaction mixture was cooled to 30° C. and water (100 g) was added to terminate the reaction. After separation of the reaction mixture into phases, the organic phase was washed with brine and an aqueous solution of sodium bicarbonate, and then concentrated under reduced pressure by removing the solvent. The residue was distilled under reduced pressure to yield (E3,Z5)-3,5-dodecadienyl acetate (bp: 92 to 96° C. [1 mmHg], 51.43 g, 0.23 mol) in a yield of 95.1%.

It was revealed by gas chromatography (DB-5: 30 m×0.25 mmϕ, temperature elevation from 150° C. to 280° C. at a rate of 10° C./min) that an EZ:EE isomer ratio was 89.65:10.35.

[Nuclear magnetic resonance spectrum] $^1$H-NMR (300 MHz, CDCl$_3$): δ 0.88(3H, t), 1.27-1.43(8H, m), 2.05(3H, s), 2.14(2H, dt), 2.43(2H, dt), 4.11(2H, t), 5.37(1H, dt), 5.60(1H, dt), 5.95(1H, dd), 6.39(1H, dd); $^{13}$C-NMR (75.6 MHz, CDCl$_3$): δ 14.10, 20.97, 22.64, 27.70, 28.94, 29.66, 31.76, 32.17, 63.80, 128.09, 128.24, 128.65, 131.56, 171.07

[Mass Spectrum] EI-mass spectrum (70 eV): m/z 165(M$^+$-59), 138, 110, 93, 80, 67; CI mass spectrum (isobutane): 225 (M+H)

[Infrared absorption spectrum] [NaCl]: vmax 3020, 2956, 2927, 2856, 1743, 1457, 1382, 1363, 1236, 1035, 983, 948

Comparative Example 1

<Reaction between 4-formyl-(E3)-3-butenyl acetate and alkylidene phosphorane (in the Case where an Alcohol is Protected with an Acetyl Group)>

Triphenylphosphine (52.51 g, 0.20 mol), n-heptane bromide (3847 g, 0.215 mol) and N,N-dimethylformamide (41.0 g) were placed in a reactor and stirred at 105 to 110° C. for 26 to 30 hours. After stirring, the reaction mixture was cooled to 20° C. and tetrahydrofuran (185.0 g) was added thereto. Then, potassium t-butoxide (21.1 g, 0.188 mol) was added at 10 to 15° C. and the resulting mixture was stirred at 20° C. for one hour. After stirring, the reaction mixture was cooled to −20° C. and 4-formyl-(E3)-3-butenyl acetate (25.87 g, 0.182 mol) was added dropwise thereto at −15 to −5° C.

After dropwise addition, the temperature of the mixture was raised to the range of 20 to 25° C. over one hour and the mixture was stirred as it was for one hour. Then, water (100 g) was added to terminate the reaction. The reaction mixture was extracted with toluene (100 g). the organic phase was washed with water and then concentrated under reduced pressure by removing toluene.

After concentration, n-hexane (120 g) was added and triphenylphosphine oxide thus precipitated was separated by filtration. The filtrate was concentrated under reduced pressure again and the concentrated solution was distilled under reduced pressure to yield intended (E3,Z5)-3,5-dodecadienyl acetate (9.80 g, 0.04 mol) in a yield of 24.0% and 1,3,5-decatriene (9.87 g, 0.06 mol) in a yield of 33.0%.

Comparative Example 2

<Preparation of 4-formyl-(E3)-3-butenyl 1-ethoxyethyl ether (in the Case where an Alcohol is Protected with a 1-ethoxyethyl Group)>

A toluene (80.0 g) solution of 5,5-dimethoxy-(Z3)-3-pentenyl 1-ethoxyethyl ether (30.0 g, 0.122 mol) was placed in a reactor and stirred at 5 to 10° C. A 5% by weight aqueous solution of acetic acid was added dropwise thereto at 10 to 15° C. and the mixture was stirred for two hours. After stirring, toluene (100 g) was added thereto to separate the mixture into phases. The water phase was removed, while the orgnanic phase was washed with brine and an aqueous solution of sodium bicarbonate.

The organic layer thus obtained was concentrated under reduced pressure by removing the solvent, and then the residue was distilled under reduced pressure to yield 2-hydroxy- 5,6-dihydropyrane (8.64 g, 0.09 mol) in a yield of 70.7%. Formation of intended 4-formyl-3-butenyl 1-ethoxyethyl ether was not observed.

Comparative Example 3

<Preparation of 4-formyl-(E3)-3-butenyl tetrahydropyranyl ether (in the Case where an Alcohol is Protected with a tetrahydropyranyl Group)>

A n-hexane (50.0 g) solution of 5,5-dimethoxy-(Z3)-3-pentenyl 1-tetrahydropyranyl ether (51.7 g, 0.20 mol) was placed in a reactor and stirred at 10 to 15° C. A 15% by weight aqueous solution (30.0 g) of acetic acid was added dropwise thereto at 15 to 20° C. and the mixture was stirred for one hour. After stirring, n-hexane (80 g) was added thereto to separate the reaction mixture into phases. The water phase was removed, while the organic phase was washed with brine and an aqueous solution of sodium bicarbonate.

The organic phase thus obtained was concentrated under reduced pressure by removing the solvent and the residue was analyzed by gas chromatography (DB-WAX: 30 m×0.25 mmϕ, temperature elevation from 150° C. to 280° C. at a rate of 10° C./min). As a result, it was found that the residue contained 9.8 GC % of 4-formyl-(E3)-3-butenyl tetrahydropyranyl ether.

The invention claimed is:

1. A method for preparing a (E3, Z5)-3,5-alkadienyl acetate, comprising steps of:

hydrolyzing 5,5-diethoxy-(Z)-3-pentenyl methoxymethyl ether in the presence of an acid to obtain 4-formyl-(E3)-butenyl methoxymethyl ether;

reacting the 4-formyl-(E3)-butenyl methoxymethyl ether with alkylidene triphenylphosphorane in accordance with the Wittig reaction to obtain (E3, Z5)-3,5-alkadienyl methoxymethyl ether; and obtaining (E3, Z5)-3,5-alkadienyl acetate from the (E3, Z5)-3,5-alkadienyl methoxymethyl ether.

2. The method for preparing a (E3, Z5)-3,5-alkadienyl acetate according to claim 1, wherein said alkylidene triphenylphosphorane is represented by RCH=PPh$_3$ wherein R represents a group having from 4 to 12 carbon atoms and Ph represents a phenyl group, and said (E3, Z5)-3,5-alkadienyl methoxymethyl ether is represented by RCH=CH—CH=CH—CH$_2$—CH$_2$—OCH$_2$OCH$_3$.

3. The method for preparing a (E3, Z5)-3,5-alkadienyl acetate according to claim 1, wherein said (E3, Z5)-3,5-alkadienyl acetate is (E3, Z5)-3,5-dodecadienyl acetate.

* * * * *

UNITED STATES PATENT AND TRADEMARK OFFICE
CERTIFICATE OF CORRECTION

| | | |
|---|---|---|
| PATENT NO. | : 7,638,647 B2 | Page 1 of 1 |
| APPLICATION NO. | : 12/323823 | |
| DATED | : December 29, 2009 | |
| INVENTOR(S) | : Yamashita et al. | |

It is certified that error appears in the above-identified patent and that said Letters Patent is hereby corrected as shown below:

<u>Column 2,</u>

Line 14, after "3-butenyl" insert --methoxymethyl--.

<u>Column 3,</u>

Line 42, in the formula, "$CH_2MgCl$" should read --$CH_3MgCl$--.

Signed and Sealed this

Fourteenth Day of September, 2010

David J. Kappos
*Director of the United States Patent and Trademark Office*